United States Patent
Gomez et al.

(10) Patent No.: US 9,155,304 B2
(45) Date of Patent: Oct. 13, 2015

(54) SYNERGISTIC PESTICIDAL COMPOSITIONS AND RELATED METHODS

(71) Applicant: Dow AgroSciences LLC, Indianapolis, IN (US)

(72) Inventors: Luis E. Gomez, Carmel, IN (US); Ricky Hunter, Westfield, IN (US); Mike Shaw, Carmel, IN (US); Tony K. Trullinger, Westfield, IN (US); Mary E. Kubiszak, Thorntown, IN (US); John Herbert, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/517,747

(22) Filed: Oct. 17, 2014

(65) Prior Publication Data

US 2015/0111745 A1 Apr. 23, 2015

Related U.S. Application Data

(60) Provisional application No. 61/894,167, filed on Oct. 22, 2013.

(51) Int. Cl.
| | | |
|---|---|---|
| A01N 43/00 | (2006.01) | |
| A61K 31/33 | (2006.01) | |
| A01N 43/56 | (2006.01) | |
| A01N 43/90 | (2006.01) | |

(52) U.S. Cl.
CPC .............. *A01N 43/56* (2013.01); *A01N 43/90* (2013.01)

(58) Field of Classification Search
None
See application file for complete search history.

(56) References Cited

U.S. PATENT DOCUMENTS

| | | | |
|---|---|---|---|
| 4,080,457 | A | 3/1978 | Harrison et al. |
| 4,260,765 | A | 4/1981 | Harrison et al. |
| 4,536,506 | A | 8/1985 | Marcoux et al. |
| 5,625,074 | A | 4/1997 | Daum et al. |
| 5,631,380 | A | 5/1997 | Haas et al. |
| 5,652,372 | A | 7/1997 | Muller et al. |
| 5,693,657 | A | 12/1997 | Lee et al. |
| 5,750,718 | A | 5/1998 | Muller et al. |
| 5,817,677 | A | 10/1998 | Linz et al. |
| 5,854,264 | A | 12/1998 | Anthony et al. |
| 5,854,265 | A | 12/1998 | Anthony |
| 5,869,681 | A | 2/1999 | Muller et al. |
| 6,218,418 | B1 | 4/2001 | Pevarello et al. |
| 6,548,525 | B2 | 4/2003 | Galemmo, Jr. et al. |
| 6,720,427 | B2 | 4/2004 | Sanner et al. |
| 6,878,196 | B2 | 4/2005 | Harada et al. |
| 6,916,927 | B2 | 7/2005 | Bunnage et al. |
| 7,192,906 | B2 | 3/2007 | Hirohara et al. |
| 7,196,104 | B2 | 3/2007 | Askew, Jr. et al. |
| 7,319,108 | B2 | 1/2008 | Schwink et al. |
| 7,774,978 | B2 | 8/2010 | Ding et al. |
| 7,803,832 | B2 | 9/2010 | Critcher et al. |
| 7,910,606 | B2 | 3/2011 | Nazare et al. |
| 7,923,573 | B2 | 4/2011 | Tamaki et al. |
| 8,163,756 | B2 | 4/2012 | Flynn et al. |

(Continued)

FOREIGN PATENT DOCUMENTS

| | | |
|---|---|---|
| EP | 0097323 | 1/1984 |
| EP | 0205024 | 12/1986 |

(Continued)

OTHER PUBLICATIONS

PCT International Search Report; PCT/US2014/061155; dated Jan. 14, 2015.

(Continued)

*Primary Examiner* — Alton Pryor
(74) *Attorney, Agent, or Firm* — Carl D. Corvin; Traskbritt, P.C.

(57) ABSTRACT

A pesticidal composition comprises a synergistically effective amount of a chloride channel activator compound and a pesticide selected from N-(3-chloro-1-(pyridin-3-yl)-1H-pyrazol-4-yl)-N-ethyl-((3,3,3-trifluoropropyl)thio) propanamide (I), N-(3-chloro-1-(pyridine-3-yl)-1H-pyrazol-4-yl)-N-ethyl-((3,3,3-trifluoropropyl) sulfinyl)propanamide (II), or any agriculturally acceptable salt thereof. A method of controlling pests comprises applying the pesticidal composition near a population of pests. A method of protecting a plant from infestation and attack by pests comprises contacting the plant with the synergistic pesticidal composition.

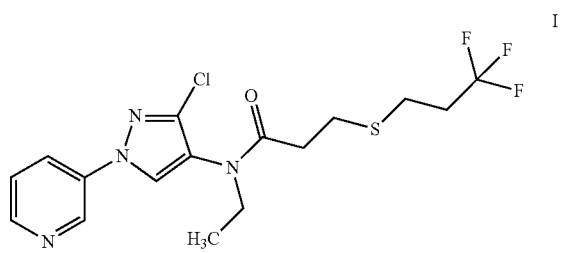

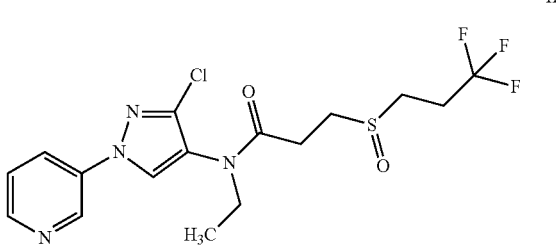

28 Claims, No Drawings

(56) References Cited

U.S. PATENT DOCUMENTS

| | | | |
|---|---|---|---|
| 8,222,280 B2 | 7/2012 | Liu et al. | |
| 8,901,153 B2 * | 12/2014 | Buysse et al. | 514/341 |
| 2002/0013326 A1 | 1/2002 | Tiebes et al. | |
| 2003/0153464 A1 | 8/2003 | Nakamura et al. | |
| 2003/0213405 A1 | 11/2003 | Harada et al. | |
| 2004/0082629 A1 | 4/2004 | Iwataki et al. | |
| 2005/0038059 A1 | 2/2005 | Mueller et al. | |
| 2005/0176710 A1 | 8/2005 | Schwink et al. | |
| 2006/0160857 A1 | 7/2006 | Buettelmann et al. | |
| 2006/0160875 A1 | 7/2006 | Gaines et al. | |
| 2007/0167426 A1 | 7/2007 | Siddiqui et al. | |
| 2008/0004301 A1 | 1/2008 | Tamaki et al. | |
| 2008/0027046 A1 | 1/2008 | Annan et al. | |
| 2009/0069288 A1 | 3/2009 | Breinlinger et al. | |
| 2009/0137524 A1 | 5/2009 | Billen et al. | |
| 2009/0325956 A1 | 12/2009 | Taniguchi et al. | |
| 2010/0130474 A1 | 5/2010 | Bothmann et al. | |
| 2010/0204164 A1 | 8/2010 | Crouse et al. | |
| 2010/0292253 A1 | 11/2010 | Trullinger et al. | |
| 2010/0305200 A1 | 12/2010 | Velicelebi et al. | |
| 2011/0021771 A1 | 1/2011 | Mallais et al. | |
| 2011/0098287 A1 | 4/2011 | Bretschneider et al. | |
| 2011/0118290 A1 | 5/2011 | Bretschneider et al. | |
| 2011/0166129 A1 | 7/2011 | Machacek et al. | |
| 2011/0166143 A1 | 7/2011 | Bretschneider et al. | |
| 2011/0184188 A1 | 7/2011 | Wada et al. | |
| 2011/0201649 A1 | 8/2011 | Matsuzaki et al. | |
| 2011/0212949 A1 | 9/2011 | Bretschneider et al. | |
| 2011/0275583 A1 | 11/2011 | Bretschneider et al. | |
| 2011/0319428 A1 | 12/2011 | Fu Lein et al. | |
| 2012/0053146 A1 | 3/2012 | Parker et al. | |
| 2012/0094837 A1 | 4/2012 | Muhlthau et al. | |
| 2012/0095023 A1 | 4/2012 | Bretschneider et al. | |
| 2012/0110701 A1 | 5/2012 | Garizi et al. | |
| 2012/0110702 A1 | 5/2012 | Yap et al. | |
| 2012/0115811 A1 | 5/2012 | Du et al. | |
| 2012/0165345 A1 | 6/2012 | Bretschneider et al. | |
| 2012/0220453 A1 | 8/2012 | Lowe et al. | |
| 2013/0072382 A1 | 3/2013 | Trullinger et al. | |
| 2013/0089622 A1 | 4/2013 | Trullinger et al. | |
| 2013/0109566 A1 | 5/2013 | Niyaz et al. | |
| 2013/0261141 A1 | 10/2013 | Bretschneider et al. | |
| 2013/0288893 A1 | 10/2013 | Buysse et al. | |
| 2013/0291227 A1 | 10/2013 | Buysse et al. | |
| 2013/0324736 A1 | 12/2013 | Ross, Jr. et al. | |
| 2013/0324737 A1 | 12/2013 | Ross, Jr. et al. | |

FOREIGN PATENT DOCUMENTS

| | | |
|---|---|---|
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 153273 | 7/1987 |
| JP | 174905 | 7/1988 |
| JP | 226815 | 9/1989 |
| JP | 2003212864 | 7/2003 |
| JP | 2004051628 | 2/2004 |
| JP | 2004292703 | 10/2004 |
| JP | 2012188418 | 10/2012 |
| JP | 2013075871 | 4/2013 |
| JP | 2013082699 | 5/2013 |
| JP | 2013082704 | 5/2013 |
| JP | 2013107867 | 6/2013 |
| JP | 2013129651 | 7/2013 |
| JP | 2013129653 | 7/2013 |
| WO | 9413644 | 6/1994 |
| WO | 9736897 | 10/1997 |
| WO | 9821199 | 5/1998 |
| WO | 9849166 | 11/1998 |
| WO | 0035919 | 6/2000 |
| WO | 0134127 | 5/2001 |
| WO | 0190078 | 11/2001 |
| WO | 02083111 | 10/2002 |
| WO | 03008405 | 1/2003 |
| WO | 03072102 | 9/2003 |
| WO | 2004041813 | 5/2004 |
| WO | 2005070925 | 8/2005 |
| WO | 2005074875 | 8/2005 |
| WO | 2006023462 | 3/2006 |
| WO | 2006033005 | 3/2006 |
| WO | 2006046593 | 5/2006 |
| WO | 2011003065 | 1/2011 |
| WO | 2011043371 | 4/2011 |
| WO | 2011045224 | 4/2011 |
| WO | 2011045240 | 4/2011 |
| WO | 2011091153 | 7/2011 |
| WO | 2011101229 | 8/2011 |
| WO | 2011126903 | 10/2011 |
| WO | 2011128304 | 10/2011 |
| WO | 2011134964 | 11/2011 |
| WO | 2011138285 | 11/2011 |
| WO | 2011163518 | 12/2011 |
| WO | 2012000896 | 1/2012 |
| WO | 2012004217 | 1/2012 |
| WO | 2012007500 | 1/2012 |
| WO | 2012035011 | 3/2012 |
| WO | 2012052412 | 4/2012 |
| WO | 2012061290 | 5/2012 |
| WO | 2012070114 | 5/2012 |
| WO | 2012102387 | 8/2012 |
| WO | 2012108511 | 8/2012 |
| WO | 2012168361 | 12/2012 |
| WO | 2012175474 | 12/2012 |
| WO | 2013000931 | 1/2013 |
| WO | 2013010946 | 1/2013 |
| WO | 2013010947 | 1/2013 |
| WO | 2013062980 | 5/2013 |
| WO | 2013156431 | 10/2013 |
| WO | 2013156433 | 10/2013 |
| WO | 2013162716 | 10/2013 |

OTHER PUBLICATIONS

PCT Written Opinion; PCT/US2014/061155; dated Jan. 14, 2015.

* cited by examiner

SYNERGISTIC PESTICIDAL COMPOSITIONS AND RELATED METHODS

CROSS-REFERENCE TO RELATED APPLICATION

This application claims the benefit of the filing date of U.S. Provisional Patent Application Ser. No. 61/894,167, filed Oct. 22, 2013, for "SYNERGISTIC PESTICIDAL COMPOSITIONS AND RELATED METHODS," pending, the disclosure of which is hereby incorporated herein in its entirety by this reference.

TECHNICAL FIELD

This disclosure relates to the field of compounds having pesticidal utility against pests in Phyla Nematoda, Arthropoda, and/or Mollusca, processes to produce such compounds and intermediates used in such processes. These compounds may be used, for example, as nematicides, acaricides, miticides, and/or molluscicides.

BACKGROUND

Controlling pest populations is essential to human health, modern agriculture, food storage, and hygiene. There are more than ten thousand species of pests that cause losses in agriculture and the worldwide agricultural losses amount to billions of U.S. dollars each year. Accordingly, there exists a continuous need for new pesticides and for methods of producing and using such pesticides.

The Insecticide Resistance Action Committee (IRAC) has classified insecticides into categories based on the best available evidence of the mode of action of such insecticides. Insecticides in the IRAC Mode of Action Group 6 are chloride channel activators. The insecticides in this class are believed to allosterically activate glutamate-gated chloride channels (GluCls), causing paralysis of the affected insects. Glutamate has been reported an important inhibitory neurotransmitter in insects. The insecticides in this class may be avermectins-based compounds or milbemycins-based compounds. Examples of these insecticides may include abamectin, emamectin benzoate, lepimectin, or milbemectin.

Emamectin benzoate is a 4'-deoxy-4'-methyl-amino benzoate salt of avermectin B1 (abamectin). Abamectin is a mixture of avermectins containing more than 80% of avermectin B1a, which is (10E,14E,16E)-(1R,4S,5'S,6S,6'R,8R,12S, 13S,20R, 21R,24S)-6'-[(S)-sec-butyl]-21,24-dihydroxy-5', 11,13,22-tetramethyl-2-oxo-(3,7,19-trioxatetracyclo [15.6.1.1$^{4,8}$.0$^{20,24}$, ]pentacosa-10,14,16,22-tetraene)-6-spiro-2'-(5',6'-dihydro-2'H-pyran)-12-yl 2,6-dideoxy-3-O-methyl-4-O-(2,4,6-trideoxy-3-O-methyl-4-methylamino-α-L-lyxo-hexapyranosyl)-α-L-arabino-hexapyranoside, and less than 20% of avermectin B1b, which is (10E,14E,16E)-(1R,4S,5'S,6S,6'R,8R,12S, 13S,20R,21R,24S)-21,24-dihydroxy-6'-isopropyl-5', 11,13,22-tetramethyl-2-oxo-(3,7,19-trioxa tetracyclo[15.6.1.1$^{4,8}$.0$^{20,24}$]pentacosa-10,14,16,22-tetraene)-6-spiro-2'-(5',6'-dihydro-2'H-pyran)-12-yl-2,6-dideoxy-3-O-methyl-4-O-(2,4,6-trideoxy-3-O-methyl-4-methylamino-α-L-lyxo-hexapyranosyl)-α-L-arabino-hexapyranoside.

Although the rotational application of pesticides having different modes of action may be adopted for good pest management practice, this approach does not necessarily give satisfactory insect control. Furthermore, even though combinations of pesticides have been studied, a high synergistic action has not always been found.

DETAILED DESCRIPTION

As used herein, the term "synergistic effect" or grammatical variations thereof means and includes a cooperative action encountered in a combination of two or more active compounds in which the combined activity of the two or more active compounds exceeds the sum of the activity of each active compound alone.

The term "synergistically effective amount," as used herein, means and includes an amount of two or more active compounds that provides a synergistic effect defined above.

The term "pesticidally effective amount," as used herein, means and includes an amount of active pesticide that causes an adverse effect to the at least one pest, wherein the adverse effect may include deviations from natural development, killing, regulation, or the like.

As used herein, the term "control" or grammatical variations thereof means and includes regulating the number of living pests or regulating the number of viable eggs of the pests or both.

The term "chloride channel activator compound," as used herein, means and includes any insecticides that are classified by the Insecticide Resistance Action Committee (IRAC), based on the best available evidence of the mode of action, to be within the IRAC Mode of Action Group 6.

In one particular embodiment, a pesticidal composition comprises a synergistically effective amount of a chloride channel activator compound in combination with a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3-trifluoropropyl)sulfinyl)propanamide (II), or any agriculturally acceptable salt thereof.

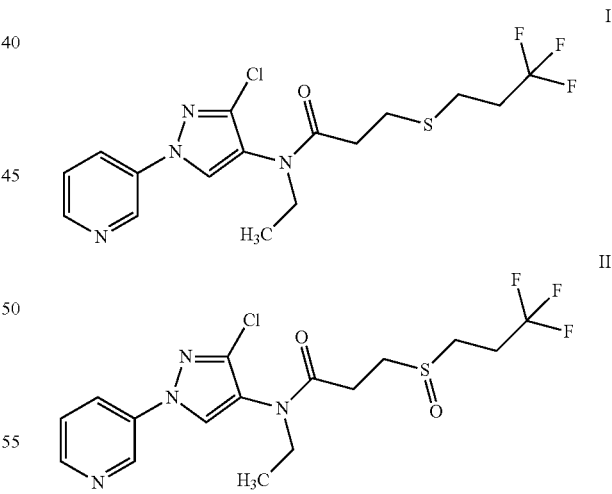

It is appreciated that a pesticide selected from N-(3-chloro-1-(pyridin-3-yl)-1H-pyrazol-4-yl)-N-ethyl-3-((3,3,3-trifluoropropyl)thio) propanamide (I), N-(3-chloro-1-(pyridin-3 -yl)-1H-pyrazol-4-yl)-N-ethyl-3-((3,3,3-trifluoropropyl) sulfinyl)propanamide (II), or any agriculturally acceptable salt thereof may be oxidized to the corresponding sulfone in the presence of oxygen.

As shown in the examples, the existence of synergistic effect is determined using the method described in Colby S.

R., "Calculating Synergistic and Antagonistic Responses of Herbicide Combinations," Weeds, 1967, 15, 20-22.

Surprisingly, it has been found that the pesticidal composition of the present disclosure has superior pest control at lower levels of the combined concentrations of the chloride channel activator compound and the pesticide (I), (II), or any agriculturally acceptable salt thereof employed than that which may be achieved when the chloride channel activator compound and the pesticide (I), (II), or any agriculturally acceptable salt thereof are applied alone. In other words, the synergistic pesticidal composition is not a mere admixture of two active compounds resulting in the aggregation of the properties of the active compounds employed in the composition.

In some embodiments, the pesticidal compositions may comprise a synergistically effective amount of an avermectins-based compound in combination with a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3-trifluoropropyl)sulfinyl) propanamide (II) or any agriculturally acceptable salt thereof.

In other embodiments, the pesticidal compositions may comprise a synergistically effective amount of a milbemycins-based compound in combination with a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3-trifluoropropyl)sulfinyl) propanamide (II) or any agriculturally acceptable salt thereof.

In further embodiments, the pesticidal compositions may comprise a synergistically effective amount of a pesticide selected from (I), (II), or any agriculturally acceptable salt thereof in combination with at least one of abamectin, emamectin benzoate, lepimectin, and milbemectin.

In still further embodiments, the pesticidal compositions may comprise a synergistically effective amount of emamectin benzoate in combination with a pesticide selected from N-(3-chloro-1-(pyridin-3-yl)-1H-pyrazol-4-yl)-N-ethyl-3-((3,3,3-trifluoropropyl)thio) propanamide (I), N-(3-chloro-1-(pyridin-3-yl)-1H-pyrazol-4-yl)-N-ethyl-3-((3,3,3-trifluoropropyl) sulfinyl)propanamide (II) or any agriculturally acceptable salt thereof.

TABLE 1A

| No. | Range of the Weight Ratio of Pesticide I or II to Chloride Channel Activator Compound |
|---|---|
| 1 | 20:1 to 1:20 |
| 2 | 15:1 to 1:15 |
| 3 | 10:1 to 1:10 |
| 4 | 5:1 to 1:5 |
| 5 | 4:1 to 1:4 |
| 6 | 3:1 to 1:3 |
| 7 | 2:1 to 1:2 |
| 8 | 1:1 |

Table 1A shows weight ratios of the pesticide (I), (II), or any agriculturally acceptable salt thereof to the chloride channel activator compound in the synergistic pesticidal compositions. In some embodiments, the weight ratio of the pesticide to the chloride channel activator compound may be between about 20:1 and about 1:20. In some embodiments, the weight ratio of the pesticide to the chloride channel activator compound may be between about 15:1 and about 1:15. In some embodiments, the weight ratio of the pesticide to the chloride channel activator compound may be between about 10:1 and about 1:10. In some embodiments, the weight ratio of the pesticide to the chloride channel activator compound may be between about 5:1 and about 1:5. In some embodiments, the weight ratio of the pesticide to the chloride channel activator compound may be between about 4:1 and about 1:4. In some embodiments, the weight ratio of the pesticide to the chloride channel activator compound may be between about 3:1 and about 1:3. In some embodiments, the weight ratio of the pesticide to the chloride channel activator compound may be between about 2:1 and about 1:2. In some embodiments, the weight ratio of the pesticide to the chloride channel activator compound may be about 1:1. Additionally, the weight ratio limits of the pesticide to the chloride channel activator compound in the aforementioned embodiments may be interchangeable. By way of non-limiting example, the weight ratio of the pesticide to the chloride channel activator compound may be between about 1:3 and about 20:1.

TABLE 1B

| Chloride channel activator compound (Y) Parts by weight | | | | | | | | |
|---|---|---|---|---|---|---|---|---|
| 20 | X,Y | | X,Y | | | | | |
| 15 | X,Y | X,Y | | X,Y | | | | |
| 10 | X,Y | | X,Y | | | | | |
| 5 | X,Y | X,Y | X,Y | X,Y | | | | |
| 4 | X,Y | | X,Y | | X,Y | | X,Y | |
| 3 | X,Y | X,Y | | X,Y | X,Y | X,Y | | X,Y |
| 2 | X,Y | | X,Y | | X,Y | | X,Y | |
| 1 | X,Y | X,Y | X,Y | X,Y | X,Y | X,Y | X,Y | X,Y |
| | 1 | 2 | 3 | 4 | 5 | 10 | 15 | 20 |
| Pesticide (I or II) (X) Parts by weight | | | | | | | | |

Weight ratios of the pesticide (I), (II), or any agriculturally acceptable salt thereof to the chloride channel activator compound envisioned to be synergistic pesticidal compositions may be depicted as X:Y; wherein X is the parts by weight of the pesticide (I), (II), or any agriculturally acceptable salt thereof, and Y is the parts by weight of the chloride channel activator compound. The numerical range of the parts by weight for X is $0<X\leq20$ and the parts by weight for Y is $0<Y\leq20$ as shown graphically in table 1B. By way of non-limiting example, the weight ratio of the pesticide to the chloride channel activator compound may be about 20:1.

Ranges of weight ratios of the pesticide (I), (II), or any agriculturally acceptable salt thereof to the chloride channel activator compound envisioned to be synergistic pesticidal compositions may be depicted as $X_1:Y_1$ to $X_2:Y_2$, wherein X and Y are defined as above. In one particular embodiment, the range of weight ratios may be $X_1:Y_1$ to $X_2:Y_2$, wherein $X_1>Y_1$ and $X_2<Y_2$. By way of non-limiting example, the range of weight ratios of the pesticide to the chloride channel activator compound may be between about 3:1 and about 1:3. In some embodiments, the range of weight ratios may be $X_1:Y_1$ to $X_2:Y_2$, wherein $X_1>Y_1$ and $X_2>Y_2$. By way of non-limiting example, the range of weight ratios of the pesticide to the chloride channel activator compound may be between about 15:1 and about 3:1. In further embodiments, the range of weight ratios may be $X_1:Y_1$ to $X_2:Y_2$, wherein $X_1<Y_1$ and $X_2<Y_2$. By way of non-limiting example, the range of weight ratios of the pesticide to the chloride channel activator compound may be between about 1:3 and about 1:20.

Table 1C shows further weight ratios of the pesticide (I), (II), or any agriculturally acceptable salt thereof to the chloride channel activator compound in the synergistic pesticidal compositions, according to particular embodiments of present disclosure. In some particular embodiments, the weight ratio of the pesticide (I), (II), or any agriculturally acceptable salt thereof to the chloride channel activator compound may be no more than about 2048:1. In further embodiments, the weight ratio of the pesticide to the chloride channel activator compound may be no more than about 256:1. In further embodiments, the weight ratio of the pesticide to the chloride channel activator compound may be no more than about 64:1. In further embodiments, the weight ratio of the pesticide to the chloride channel activator compound may be no more than about 32:1. In yet further embodiments, the weight ratio of the pesticide to the chloride channel activator compound may be no more than about 16:1.

TABLE 1C

| Dose Rate Of Pesticide (I or II) (weight %) | Dose Rate of Chloride Channel Activator Compound (weight %) | Weight Ratio of Pesticide (I or II) to Chloride Channel Activator Compound |
|---|---|---|
| 0.04 | 0.00002 | ≤2048:1 |
| 0.04 | 0.000156 | ≤256:1 |
| 0.0025 | 0.000039 | ≤64:1 |
| 0.0025 | 0.000078 | ≤32:1 |
| 0.000625 | 0.000039 | ≤16:1 |

The weight ratio of the pesticide (I), (II), or any agriculturally acceptable salt thereof to the chloride channel activator compound in the synergistic pesticidal composition may be varied and different from those described in table 1A, table 1B, and table 1C. One skilled in the art recognizes that the synergistic effective amount of the combination of active compounds may vary accordingly to various prevailing conditions. Non-limiting examples of such prevailing conditions may include the type of pests, the type of crops, the mode of application, the application timing, the weather conditions, the soil conditions, the topographical character, or the like. It is understood that one skilled in the art may readily determine the synergistic effective amount of the chloride channel activator compound and the pesticide (I), (II), or any agriculturally acceptable salt thereof accordingly to the prevailing conditions.

In some embodiments, the pesticidal composition may comprise a synergistically effective amount of a chloride channel activator compound in combination with a pesticide selected from N-(3-chloro-1-(pyridin-3-yl)-1H-pyrazol-4-yl)-N-ethyl-3-((3,3,3-trifluoropropyl)thio) propanamide (I), N-(3-chloro-1-(pyridin-3-yl)-1H-pyrazol-4-yl)-N-ethyl-3-((3,3,3-trifluoropropyl) sulfinyl)propanamide (II), or any agriculturally acceptable salt thereof, and a phytologically-acceptable inert carrier (e.g., solid carrier, or liquid carrier).

In further embodiments, the pesticidal composition may further comprise at least one additive selected from a surfactant, a stabilizer, an emetic agent, a disintegrating agent, an antifoaming agent, a wetting agent, a dispersing agent, a binding agent, dye, filler, or combinations thereof.

In particular embodiments, each of the active compounds (a chloride channel activator compound and a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3 ((3,3,3-trifluoropropyl)sulfinyl)propanamide (II), or any agriculturally acceptable salt thereof) may be formulated separately as a wettable powder, emulsifiable concentrate, aqueous or liquid flowable, suspension concentrate or any one of the conventional formulations used for pesticides, and then tank-mixed in the field with water or other liquid for application as a liquid spray mixture. When desired, the separately formulated pesticides may also be applied sequentially.

In some embodiments, the synergistic pesticidal composition may be formulated into a more concentrated primary composition, which is then diluted with water or other diluent before use. In such embodiments, the synergistic pesticidal composition may further comprise a surface active agent.

In one particular embodiment, the method of protecting a plant from infestation and attack by pests comprises contacting the plant with a pesticidal composition comprising a synergistically effective amount of a chloride channel activator compound in combination with a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3-trifluoropropyl)sulfinyl)propanamide (II), or any agriculturally acceptable salt thereof.

In some embodiments, the pesticidal compositions may be in the form of solid. Non-limiting examples of the solid forms may include powder, dust or granular formulations.

In other embodiments, the pesticidal compositions may be in the form of liquid formulation. Examples of the liquid forms may include, but are not limited to, dispersion, suspension, emulsion or solution in appropriate liquid carrier. In particular embodiments, the synergistic pesticidal compositions may be in the form of liquid dispersion, wherein the synergistic pesticidal compositions may be dispersed in water or other agriculturally suitable liquid carrier.

In certain embodiments, the synergistic pesticidal compositions may be in the form of solution in an appropriate organic solvent. In one embodiment, the spray oils, which are widely used in agricultural chemistry, may be used as the organic solvent for the synergistic pesticidal compositions.

In one particular embodiment, the method of controlling pests comprises applying a pesticidal composition near a population of pests, wherein the pesticidal composition comprises a synergistically effective amount of a chloride channel activator compound in combination with a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3-trifluoropropyl)sulfinyl)propanamide (II), or any agriculturally acceptable salt thereof.

In some embodiments, the method of controlling pests comprises applying a pesticidal composition near a population of pests, wherein the pesticidal composition comprises a synergistically effective amount of an avermectins-based or a milbemycins-based compound in combination with a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3-trifluoropropyl)sulfinyl)propanamide (II) or any agriculturally acceptable salt thereof.

In other embodiments, the method of controlling pests comprises applying a pesticidal composition near a population of pests, wherein the pesticidal composition comprises a synergistically effective amount of the pesticide in combination with at least one of abamectin, emamectin benzoate, lepimectin, and milbemectin.

In further embodiments, the method of controlling pests comprises applying a pesticidal composition near a population of pests, wherein the pesticidal composition comprises a synergistically effective amount of emamectin benzoate in combination with a pesticide selected from N-(3-chloro-1-(pyridin-3-yl)-1H-pyrazol-4-yl)-N-ethyl-3-((3,3,3-trifluoropropyl) thio) propanamide (I), N-(3-chloro-1-(pyridin-3-yl)-1H-pyrazol-4-yl)-N-ethyl-3-((3,3,3-trifluoropropyl) sulfinyl) propanamide (II) or any agriculturally acceptable salt thereof.

The control of pests may be achieved by applying a pesticidally effective amount of the synergistic pesticidal compositions in form of sprays, topical treatment, gels, seed coatings, microcapsulations, systemic uptake, baits, eartags, boluses, foggers, fumigants aerosols, dusts, or the like.

These disclosed pesticidal compositions may be used, for example, as nematicides, acaricides, miticides, and/or molluscicides.

The pesticidal composition of the present disclosure may be used to control a wide variety of insects. As a non-limiting example, in one or more embodiments, the pesticidal composition may be used to control one or more members of at least one of Phylum Arthropoda, Phylum Nematoda, Subphylum Chelicerata, Subphylum Myriapoda, Subphylum Hexapoda, Class Insecta, Class Arachnida, and Class Symphyla. In at least some embodiments, the method of the present disclosure may be used to control one or more members of at least one of Class Insecta and Class Arachnida.

As a non-limiting example, in one or more embodiments, the method of the present disclosure may be used to control one or more members of at least one of Phylum Arthropoda, Phylum Nematoda, Subphylum Chelicerata, Subphylum Myriapoda, Subphylum Hexapoda, Class Insecta, Class Arachnida, and Class Symphyla. In at least some embodiments, the method of the present disclosure may be used to control one or more members of at least one of Class Insecta and Class Arachnida.

In additional embodiments, the method of the present disclosure may be used to control members of the Order Coleoptera (beetles) including, but not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass *Ataenius*), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomelids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysomelids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus suninamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana* (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In other embodiments, the method of the present disclosure may also be used to control members of the Order Dermaptera (earwigs).

In additional embodiments, the method of the present disclosure may be used to control members of the Order Dictyoptera (cockroaches) including, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In further embodiments, the method of the present disclosure may be used to control members of the Order Diptera (true flies) including, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Bactrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Liriomyza sativae* (vegetable leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In other embodiments, the method of the present disclosure may be used to control members of the Order Hemiptera Sub-order Heteroptera (true bugs) including, but is not limited to, *Acrosternum hilare* (green stink bug), *Blissus leucopterus* (chinch bug), *Bragada hilaris, Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros*,

*Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Lygus lineolaris* (tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildinii* (redbanded stink bug), *Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In additional embodiments, the method of the present disclosure may be used to control members of the Order Hemiptera, Sub-orders Auchenorrhyncha (Free-living Hemipterans) and Sternorrhyncha (Plant-parasitic Hemipterans) (aphids, scales, whiteflies, leafhoppers) including, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Chrysomphalus aonidum* (Florida red scale) *Coccus* spp. (scales), *Coccus pseudomagnoliarum* (citricola scale), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus* spp., *Myzus persicae* (green peach aphid), *Nephotettix* spp. (leafhoppers), *Nephotettix cinctipes* (green leafhopper), *Nilaparvata lugens* (brown planthopper), *Paratrioza cockerelli* (tomato psyllid), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Planococcus citri* (citrus mealybug), *Planococcus ficus* (grape mealybug), *Pseudococcus* spp. (mealybugs), *Pseudococcus brevipes* (pine apple mealybug), *Quadraspidiotus perniciosus* (San Jose scale), *Rhopalosiphum* spp. (aphids), *Rhopalosiphum maidis* (corn leaf aphid), *Rhopalosiphum padi* (oat birdcherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*. In at least some embodiments, the method of the present disclosure may be used to control *Myzus persicae*.

In other embodiments, the method of the present disclosure may be used to control members of the Order Hymenoptera (ants, wasps, and sawflies) including, but not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* spp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In certain embodiments, the method of the present disclosure may be used to control members of the Order Isoptera (termites) including, but not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In additional embodiments, the method of the present disclosure may be used to control members of the Order Lepidoptera (moths and butterflies) including, but not limited to, *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydiafunebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella*, *Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant tortrix), *Pandemis heparana* (brown apple tortrix), *Papilio demodocus*, *Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella*, *Phyllonorycter* spp. (leafminers), *Pieris rapae* (imported cabbageworm), *Plathypena scabra*, *Plodia interpunctella* (Indian meal moth), *Plutella xylostella* (diamondback moth), *Polychrosis viteana* (grape berry moth), *Prays endocarps*, *Prays oleae* (olive moth), *Pseudaletia* spp. (noctuid moths), *Pseudaletia unipunctata* (armyworm), *Pseudoplusia includens* (soybean looper), *Rachiplusia nu*, *Scirpophaga incertulas*, *Sesamia* spp. (stemborers), *Sesamia inferens* (pink rice stem borer), *Sesamia nonagrioides*, *Setora nitens*, *Sitotroga cerealella* (Angoumois grain moth), *Sparganothis pilleriana*, *Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides*, *Thermisia gemmatalis*, *Tineola bisselliella* (webbing clothes moth), *Trichoplusia ni* (cabbage looper), *Tuta absoluta*, *Yponomeuta* spp., *Zeuzera coffeae* (red branch borer), and *Zeuzera pyrina* (leopard moth). In at least some embodiments, the method of the present disclosure may be used to control *Spodoptera exigua*.

The method of the present disclosure may be used to also control members of the Order Mallophaga (chewing lice) including, but not limited to, *Bovicola ovis* (sheep biting louse), *Menacanthus stramineus* (chicken body louse), and *Menopon gallinea* (common hen louse).

In additional embodiments, the method of the present disclosure may be used to control members of the Order Orthoptera (grasshoppers, locusts, and crickets) including, but not limited to, *Anabrus simplex* (Mormon cricket), *Gryllotalpidae* (mole crickets), *Locusta migratoria*, *Melanoplus* spp. (grasshoppers), *Microcentrum retinerve* (angularwinged katydid), *Pterophylla* spp. (kaydids), *chistocerca gregaria*, *Scudderia furcata* (forktailed bush katydid), and *Valanga nigricorni*.

In other embodiments, the method of the present disclosure may be used to control members of the Order Phthiraptera (sucking lice) including, but not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In particular embodiments, the method of the present disclosure may be used to control members of the Order Siphonaptera (fleas) including, but not limited to, *Ctenocephalides canis* (dog flea), *Ctenocephalides felis* (cat flea), and *Pulex irritans* (human flea).

In additional embodiments, the method of the present disclosure may be used to control members of the Order Thysanoptera (thrips) including, but not limited to, *Caliothrips fasciatus* (bean thrips), *Caliothrips phaseoli*, *Frankliniella fusca* (tobacco thrips), *Frankliniella occidentalis* (western flower thrips), *Frankliniella shultzei*, *Frankliniella williamsi* (corn thrips), *Heliothrips haemorrhaidalis* (greenhouse thrips), *Riphiphorothrips cruentatus*, *Scirtothrips* spp., *Scirtothrips citri* (citrus thrips), *Scirtothrips dorsalis* (yellow tea thrips), *Taeniothrips rhopalantennalis*, *Thrips* spp., *Thrips tabaci* (onion thrips), and *Thrips hawaiiensis* (Hawaiian flower thrips).

The method of the present disclosure may be used to also control members of the Order Thysanura (bristletails) including, but not limited to, *Lepisma* spp. (silverfish) and *Thermobia* spp. (firebrats).

In further embodiments, the method of the present disclosure may be used to control members of the Order Acari (mites and ticks) including, but not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi*, *Aculus pelekassi*, *Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati*, *Oligonychus* spp., *Oligonychus coffee*, *Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae*, *Tetranychus* spp., *Tetranychus urticae* (twospotted spider mite), and *Varroa destructor* (honey bee mite).

In additional embodiments, the method of the present disclosure may be used to control members of the Order Nematoda (nematodes) including, but not limited to, *Aphelenchoides* spp. (foliar nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In at least some embodiments, the method of the present disclosure may be used to control at least one insect in one or more of the Orders Lepidoptera, Coleoptera, Hemiptera, Thysanoptera, Isoptera, Orthoptera, Diptera, Hymenoptera, and Siphonaptera, and at least one mite in the Order Acari.

In some embodiments, the method of controlling an insect may comprise applying a pesticidal composition near a population of pests, wherein the pesticidal composition comprises a synergistically effective amount of a chloride channel activator compound in combination with a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3- trifluoropropyl)sulfinyl)propanamide (II) or any agriculturally acceptable salt thereof, and wherein the pests comprise sap feeding insects, chewing insects, or both.

In other embodiments, the method of controlling an insect may comprise applying a pesticidal composition near a population of pests, wherein the pesticidal composition comprises a synergistically effective amount of a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3-trifluoropropyl)sulfinyl)propanamide (II) or any agriculturally acceptable salt thereof, and at least one of abamectin, emamectin benzoate, lepimectin, and milbemectin, wherein the pests comprise sap feeding insects, chewing insects, or both.

In further embodiments, the method of controlling an insect may comprise applying a pesticidal composition near a population of pests, wherein the pesticidal composition comprises a synergistically effective amount of an avermectins-based or a milbemycins-based compound in combination with a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3-trifluoropropyl)sulfinyl)propanamide (II) or any agriculturally acceptable salt thereof, wherein the pests comprise at least one of diamondback moth, *Plutella xylostella*; South American brown stink bug, *Euschistus heros*; and Western plant bug, *Lygus Hesperus*.

In yet further embodiments, the method of controlling an insect may comprise applying a pesticidal composition near a population of pests, wherein the pesticidal composition comprises a synergistically effective amount of emamectin benzoate and a pesticide selected from N-(3-chloro-1-(pyridin-3-yl)-1H-pyrazol-4-yl)-N-ethyl-3-((3,3,3-trifluoropropyl)thio)propanamide (I), N-(3-chloro-1-(pyridin-3-yl)-1H-pyrazol-4-yl)-N-ethyl-3-((3,3,3-trifluoropropyl)sulfinyl)propanamide (II), or any agriculturally acceptable salt thereof, and wherein the pests comprise at least one of diamondback moth, *Plutella xylostella*; South American brown stink bug, *Euschistus heros*; and Western plant bug, *Lygus Hesperus*.

In one embodiment of present disclosure, the pesticidal composition may be used in conjunction (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, and/or virucidal properties.

In another embodiment of present disclosure, the pesticidal composition may be used in conjunction (such as, in a compositional mixture, or a simultaneous or sequential application) with one or more compounds that are antifeedants, bird repellents, chemosterilants, herbicide safeners, insect attractants, insect repellents, mammal repellents, mating disrupters, plant activators, plant growth regulators, and/or synergists.

The pesticidal compositions of present disclosure show a synergistic effect, providing superior pest control at lower pesticidally effective amounts of the combined active compounds than when a chloride channel activator compound or a pesticide selected from N-(3-chloro-1-(pyridin-3-yl)-1H-pyrazol-4-yl)-N-ethyl-3-((3,3,3-trifluoropropyl)thio) propanamide (I), N-(3-chloro-1-(pyridin-3-yl)-1H-pyrazol-4-yl)-N-ethyl-3-((3,3,3-trifluoropropyl)sulfinyl) propanamide (II), or any agriculturally acceptable salt thereof is used alone.

The pesticidal compositions of present disclosure may have high synergistic pest control and allow for a lower effective dosage rate, an increased environmental safety, and a reduced incidence of pest resistance.

The following examples serve to explain embodiments of the present invention in more detail. These examples should not be construed as being exhaustive or exclusive as to the scope of this disclosure.

EXAMPLES

Example 1

Preparation of 3-((3,3,3-trifluoropropyl)thio)propanoyl chloride

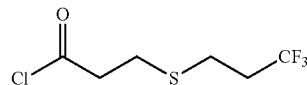

A dry five-liter round bottom flask equipped with magnetic stirrer, nitrogen inlet, reflux condenser, and thermometer, was charged with 3-((3,3,3-trifluoropropyl)thio)propanoic acid (prepared as described in the PCT Publication No. WO 2013/062981 to Niyaz et al.) (188 g, 883 mmol) in dichloromethane ($CH_2Cl_2$) (3 L). Thionyl chloride (525 g, 321 mL, 4.42 mol) was added dropwise over 50 minutes. The reaction mixture was heated to reflux (about 36° C.) for two hours, then cooled to room temperature (about 22° C.). The resulting mixture was concentrated under vacuum on a rotary evaporator, followed by distillation (40 Torr, product collected at a temperature of from about 123° C. to about 127° C.) to provide the title compound as a clear colorless liquid (177.3 g, 86%): $^1$H NMR (400 MHz, $CDCl_3$) δ 3.20 (t, J=7.1 Hz, 2H), 2.86 (t, J=7.1 Hz, 2H), 2.78-2.67 (m, 2H), 2.48-2.31 (m, 2H); $^{19}$F NMR (376 MHz, $CDCl_3$) δ −66.42, −66.43, −66.44, −66.44.

Example 2

Preparation of N-(3-chloro-1-(pyridin-3-yl)-1H-pyrazol-4-yl)-N-ethyl-3-((3,3,3-trifluoropropyl)thio) propanamide(I)

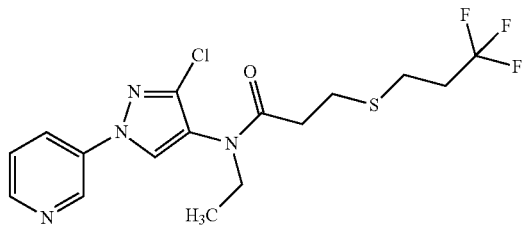 [SMILES: CCN(C(=O)CCSCCC(F)(F)F)c1cn(-c2cccnc2)nc1Cl]

To a solution of 3-chloro-N-ethyl-1-(pyridin-3-yl)-1H-pyrazol-4-amine (prepared as described in the U.S. Publication No. 2012/0110702 to Yap et al.) (10 g, 44.9 mmol) in $CH_2Cl_2$ (100 mL) at a temperature of about 0° C. and under $N_2$ was added pyridine (5.45 mL, 67.4 mmol), 4-dimethylaminopyridine (DMAP) (2.74 g, 22.45 mmol), and 3-((3,3,3-trifluoropropyl)thio) propanoyl chloride (9.91 g, 44.9 mmol), sequentially. The reaction was warmed to room temperature and stirred for one hour. The reaction mixture was poured into water (100 mL), and the resulting mixture was stirred for five minutes. The mixture was transferred to a separatory funnel, and the layers were separated. The aqueous phase was extracted with $CH_2Cl_2$ (3×50 mL), and the combined organic extracts were dried over sodium sulfate ($Na_2SO_4$), filtered, and concentrated in vacuo. The crude product was purified via normal phase flash chromatography (0% to 100% EtOAc/$CH_2Cl_2$) to provide the desired product as a pale yellow solid (17.21 g, 89%): IR (thin film) 1659 $cm^{-1}$; $^1$H NMR (400 MHz, $CDCl_3$) δ 8.95 (d, J=2.6 Hz, 1H), 8.63 (dd, J=4.7, 1.3 Hz, 1H), 8.05 (ddd, J=8.3, 2.7, 1.4 Hz, 1H), 7.96 (s, 1H), 7.47 (dd, J=8.3, 4.8 Hz, 1H), 3.72 (q, J=7.1 Hz, 2H), 2.84 (t, J=7.2 Hz, 2H), 2.66 (m, 2H), 237 (t, J=7.2 Hz, 2H), 2.44 (m, 2H), 1.17 (t, J=7.2 Hz, 3H); ESIMS m/z 409 ([M+2H]$^+$).

Example 3

Preparation of N-(3-chloro-1-(pyridin-3-yl)-1H-pyrazol-4-yl)-N-ethyl-3-((3,3,3-trifluoropropyl)sulfinyl)propanamide(II)

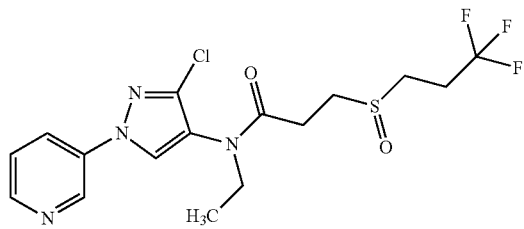

To a solution of N-(3-chloro-1-(pyridin-3-yl)-1H-pyrazol-4-yl)-N-ethyl-3-((3,3,3-trifluoropropyl)thio)propanamide (I) (500 mg, 1.229 mmol) in hexafluoroisopropanol (5 mL) stirring at room temperature was added 30% hydrogen peroxide (523 mg, 4.92 mmol). The solution was stirred at room temperature for 15 minutes. It was quenched with saturated sodium sulfite solution and extracted with $CH_2Cl_2$. Silica gel chromatography (0%-10% MeOH/$CH_2Cl_2$) gave the title compound as white semi-solid (495 mg, 95%): IR (thin film) 1660 $cm^{-1}$; $^1$H NMR (400 MHz, $CDCl_3$) δ 8.96 (d, J=2.4 Hz, 1H), 8.64 (dd, J=4.7, 1.4 Hz, 1H), 8.07-8.00 (m, 2H), 7.46 (ddd, J=8.3, 4.8, 0.7 Hz, 1H), 3.85-3.61 (m, 2H), 3.23-3.08 (m, 1H), 3.03-2.76 (m, 3H), 2.74-2.52 (m, 4H), 1.18 (t, J=7.2 Hz, 3H); ESIMS m/z 423 ([M+H]$^+$).

Example 4

Determination of the Existence of Synergic Effect

The method described in Colby S. R., "Calculating Synergistic and Antagonistic Responses of Herbicide Combinations," Weeds, 1967, 15, 20-22 was used to determine an existence of synergic effect between the chloride channel activator compound and the pesticide (I), (II), or any agriculturally acceptable salt thereof in the formulated pesticidal composition. In this method, the percent insect control of the formulated pesticidal composition as observed in the study was compared to the "expected" percent control (E) as calculated by equation (1) (hereinafter "Colby's equation") below:

$$E = X + Y - \left(\frac{XY}{100}\right) \quad (1)$$

where
- X is the percentage of control with the first pesticide at a given rate (p),
- Y is the percentage of control with the second pesticide at a given rate (q), and
- E is the expected control by the first and second pesticide at a rate of p+q.

If the observed percent control of the formulated pesticidal is greater than E, there is a synergistic effect between the chloride channel activator compound and the pesticide (I), (II), or any agriculturally acceptable salt thereof in the formulated pesticidal composition. If the observed percent control of the formulated pesticidal is equaled to or less than E, there is no synergistic effect between the chloride channel activator compound and the pesticide (I), (II), or any agriculturally acceptable salt thereof in the formulated pesticidal composition.

Example 5

Synergistic Effect of N-(3-chloro-1-(pyridin-3-yl)-1H-pyrazol-4-yl)-N-ethyl-3-((3,3,3-trifluoropropyl)thio)propanamide (I) and Emamectin Benzoate Against Diamondback Moth, *Plutella xylostella*

Example 5A

A pesticidal composition was prepared by thoroughly mixing about 0.0025 weight % of N-(3-chloro-1-(pyridin-3-yl)-1H-pyrazol-4-yl)-N-ethyl-3-((3,3,3-trifluoropropyl)thio) propanamide (hereinafter "compound I") with about 0.000078 weight % of emamectin benzoate.

Bioassays were performed for different active compounds. Cabbage plants with about two to three new-growth—true leaf stage were treated with different active compounds using a track sprayer application at 400 L/Ha spray volume. Three second instar diamondback moth, *Plutella xylostella*, were infested onto each leaf disc. The percent control determined three days after the treatment were as shown in table 2. The percent control of the pesticidal composition against diamondback moth, *Plutella xylostella*, was determined as the "Observed" action, and compared to those obtained by using about 0.0025 weight % of compound II, and using about 0.000078 weight % of emamectin benzoate alone. The "Colby's Expected Action" was calculated using Colby's equation as discussed previously.

As shown in table 2, the observed percent control of the pesticidal composition against diamondback moth (100%) was higher than the expected percentage control according to Colby's equation (91.7%). This was 9% improvement over the Colby's expected action. Therefore, the pesticidal composition comprising 0.0025 weight % of compound I and about 0.000078 weight % of emamectin benzoate showed synergistic effect against diamondback moth.

TABLE 2

| Treatment for Diamondback Moth | Dose Rate (weight %) | % Control Three Days After Treatment |
| --- | --- | --- |
| Compound I | 0.0025 | 4.35% |
| Emamectin Benzoate | 0.000078 | 91.3% |
| Compound I (+) Emamectin Benzoate Observed Action | 0.0025 + 0.000078 | 100% |
| Compound I (+) Emamectin Benzoate Colby's Expected Action | 0.0025 + 0.000078 | 91.7% |

TABLE 2-continued

| Treatment for Diamondback Moth | Dose Rate (weight %) | % Control Three Days After Treatment |
|---|---|---|
| Compound I (+) Emamectin Benzoate Differences: Observed vs. Expected | 0.0025 + 0.000078 | 8.3% |

Example 5B

A pesticidal composition was prepared by thoroughly mixing about 0.0025 weight % of compound I with about 0.000039 weight % of emamectin benzoate.

Bioassays were performed wherein different active compounds were tested against diamondback moth, *Plutella xylostella*, using the procedure described in example 5A. The percent control against diamondback moth determined three days after the treatment were as shown in table 3.

TABLE 3

| Treatment for Diamondback Moth | Dose Rate (weight %) | % Control Three Days After Treatment |
|---|---|---|
| Compound I | 0.0025 | 4.35% |
| Emamectin Benzoate | 0.000039 | 73.91% |
| Compound I (+) Emamectin Benzoate Observed Action | 0.0025 + 0.000039 | 95.65% |
| Compound I (+) Emamectin Benzoate Colby's Expected Action | 0.0025 + 0.000039 | 75.00% |
| Compound I (+) Emamectin Benzoate Differences: Observed vs. Expected | 0.0025 + 0.000039 | 20.65% |

As shown in table 3, the observed percent control of the pesticidal composition against diamondback moth (95.65%) was higher than the expected percentage control according to Colby's equation (75%). This was about 27.5% improvement over the Colby's expected action. Therefore, the pesticidal composition comprising 0.0025 weight % of compound I and about 0.000039 weight % of emamectin benzoate showed synergistic effect against diamondback moth.

Example 5C

A pesticidal composition was prepared by thoroughly mixing about 0.000625 weight % of compound I with about 0.000039 weight % of emamectin benzoate.

Bioassays were performed wherein different active compounds were tested against diamondback moth, *Plutella xylostella*, using the procedure described in example 5A. The percent control against diamondback moth determined three days after the treatment were as shown in table 4.

TABLE 4

| Treatment for Diamondback Moth | Dose Rate (weight %) | % Control Three Days After Treatment |
|---|---|---|
| Compound I | 0.000625 | 0% |
| Emamectin Benzoate | 0.000039 | 73.91% |
| Compound I (+) Emamectin Benzoate Observed Action | 0.000625 + 0.000039 | 82.61% |
| Compound I (+) Emamectin Benzoate Colby's Expected Action | 0.000625 + 0.000039 | 73.90% |
| Compound I (+) Emamectin Benzoate Differences: Observed vs. Expected | 0.000625 + 0.000039 | 8.71% |

As shown in table 4, compound I at a dose rate of 0.000625 weight % showed no control against diamondback moth three days after the treatment. Furthermore, the observed percent control of the pesticidal composition against diamondback moth (82.61%) three days after the treatment was higher than the expected percentage control according to Colby's equation (73.90%). This was about 12% improvement over the Colby's expected action. Therefore, the pesticidal composition comprising 0.000625 weight % of compound I and about 0.000039 weight % of emamectin benzoate showed synergistic effect against diamondback moth.

Example 6

Synergistic Effect of N-(3-chloro-1-(pyridin-3-yl)-1H-pyrazol-4-yl)-N-ethyl-3-((3,3,3-trifluoropropyl)thio)propanamide (I) and Emamectin Benzoate Against South American Brown Stink Bug, *Euschistus heros*

A pesticidal composition was prepared by thoroughly mixing about 0.04 weight % of compound I with about 0.000156 weight % of emamectin benzoate.

The active compounds were formulated in a 10% acetone solution with 0.025% non-ionic surfactant, TWEEN® 20. Bioassays were performed for each different active solution. Bean pieces (about one inch-long) were used for the tests. Four bean pieces were placed in each tested active solution and left there for 10 minutes. Bean pieces were taken out of the active solution, and each piece was placed in a well in a 32-well tray and allowed to air dry. Three third-instar nymphs of South American brown stink bug, *Euschistus heros*, were infested into each well. The percent control determined after four days of the treatment were as shown in table 5.

TABLE 5

| Treatment for Brown Stink Bug | Dose Rate (weight %) | % Control Four Days After Treatment |
|---|---|---|
| Compound I | 0.04 | 8% |
| Emamectin Benzoate | 0.000156 | 25% |
| Compound I (+) Emamectin Benzoate Observed Action | 0.04 + 0.000156 | 42% |
| Compound I (+) Emamectin Benzoate Colby's Expected Action | 0.04 + 0.000156 | 31% |
| Compound I (+) Emamectin Benzoate Differences: Observed vs. Expected | 0.04 + 0.000156 | 11% |

The percent control of the pesticidal composition against South American brown stink bug, *Euschistus heros*, was determined as the "Observed" action, and compared to those obtained by using about 0.04 weight % of compound I, and using about 0.000156 weight % of emamectin benzoate alone. The "Colby's Expected Action" was calculated using Colby's equation as discussed previously.

As shown in table 5, the observed percent control of the pesticidal composition against brown stink bug (42%) was higher than the expected percentage control according to Colby's equation (31%). This was 35% improvement over the Colby's expected action. Therefore, the pesticidal composition comprising 0.04 weight % of compound I and about 0.000156 weight % of emamectin benzoate showed synergistic effect against South American brown stink bug, *Euschistus heros*.

Example 7

Synergistic Effect of N-(3-chloro-1-(pyridin-3-yl)-1H-pyrazol-4-yl)-N-ethyl-3-((3,3,3-trifluoropropyl)thio)propanamide (I) and Emamectin Benzoate Against Western Plant Bug, *Lygus hesperus*

A pesticidal composition was prepared by thoroughly mixing about 0.04 weight % of compound I with about 0.20 weight % of emamectin benzoate.

The active compounds were formulated in a 10% acetone solution with 0.025% non-ionic surfactant, TWEEN® 20. Bioassays were performed for each different active solution. Bean pieces (about one inch-long) were used for the tests. Four bean pieces were placed in each tested active solution and left there for 10 minutes. Bean pieces were taken out of the active solution, and each piece was placed in a well in a 32-well tray and allowed to air dry. Three third-instar nymphs of Western plant bug, *Lygus hesperus*, were infested into each well. The percent control determined three days after the treatment were as shown in table 6. The percent control of the pesticidal composition against *Lygus hesperus* bug was determined as the "Observed" action, and compared to those obtained by using about 0.04 weight % of compound I, and using about 0.20 weight % of emamectin benzoate alone. The "Colby's Expected Action" was calculated using Colby's equation as discussed previously.

As shown in table 6, the observed percent control of the pesticidal composition against *Lygus hesperus* bug was about 17% three days after treatment. On the other hand, compound I and emamectin benzoate, when used alone, showed no control against *Lygus hesperus* bug three days after the treatment, and therefore the expected percentage control according to Colby's equation was zero. Thus, the pesticidal composition comprising 0.04 weight % of compound I and 0.20 weight % of emamectin benzoate showed synergistic effect against Western plant bug, *Lygus hesperus*.

TABLE 6

| Treatment for *Lygus hesperus* | Dose Rate (weight %) | % Control Three Days After Treatment |
| --- | --- | --- |
| Compound I | 0.04 | 0% |
| Emamectin Benzoate | 0.20 | 0% |
| Compound I (+) Emamectin Benzoate Observed Action | 0.04 + 0.20 | 17% |
| Compound I (+) Emamectin Benzoate Colby's Expected Action | 0.04 + 0.20 | 0% |
| Compound I (+) Emamectin Benzoate Differences: Observed vs. Expected | 0.04 + 0.20 | 17% |

Example 8

Synergistic Effect of N-(3-chloro-1-(pyridin-3-yl)-1H-pyrazol-4-yl)-N-ethyl-3-((3,3,3-trifluoropropyl)thio)propanamide (I) or N-(3-chloro-1-(pyridin-3-yl)-1H-pyrazol-4-yl)-N-ethyl-3-((3,3,3-trifluoropropyl)sulfinyl)propanamide (II) and Emamectin Benzoate A pesticidal composition may be prepared by thoroughly mixing compound I (weight %) or compound II (weight %) with emamectin benzoate (weight %).

The bioassays may be performed for different active compounds against Diamondback Moth, *Plutella xylostella*, using the same procedure as that described in example 5. The percent control may be determined some time after the treatment.

The bioassays may be performed for different active compounds against South American Brown Stink Bug, *Euschistus heros*, using the same procedure as that described for example 6. The percent control may be determined some time after the treatment.

The bioassays may be performed for different active compounds against Western Plant Bug, *Lygus hesperus*, using the same procedure as that described for example 7. The percent control may be determined some time after the treatment.

The observed percent control of the pesticidal composition against Diamondback Moth, *Plutella xylostella* is expected to be higher than the expected percentage control according to Colby's equation. Therefore, the pesticidal composition comprising compound I (weight %) or compound II (weight %) and emamectin benzoate (weight %) is expected to show synergistic effect against Diamondback Moth, *Plutella xylostella*.

The observed percent control of the pesticidal composition against South American Brown Stink Bug, *Euschistus heros* is expected to be higher than the expected percentage control according to Colby's equation. Therefore, the pesticidal composition comprising compound I (weight %) or compound II (weight %) and emamectin benzoate (weight %) is expected to show synergistic effect against South American Brown Stink Bug, *Euschistus heros*.

The observed percent control of the pesticidal composition against Western Plant Bug, *Lygus hesperus* is expected to be higher than the expected percentage control according to Colby's equation. Therefore, the pesticidal composition comprising compound I (weight %) or compound II (weight %) and emamectin benzoate (weight %) is expected to show synergistic effect against Western Plant Bug, *Lygus hesperus*.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

We claim:

1. A pesticidal composition comprising a synergistically effective amount of:
    a chloride channel activator compound selected from avermectins-based compound or milbemycins-based compound; and
    a pesticide selected from N-(3-chloro-1-(pyridin-3-yl)-1H-pyrazol-4-yl)-N-ethyl-3-((3,3,3-rifluoropropyl)thio)propanamide (I), N-(3-chloro-1-(pyridin-3-yl)-1H- pyrazol-4-yl)-N-ethyl-3-((3,3,3-trifluoropropyl) sulfinyl)propanamide (II), or any agriculturally acceptable salt thereof.

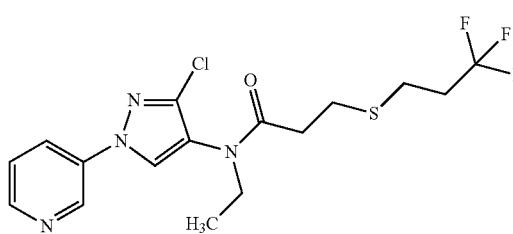

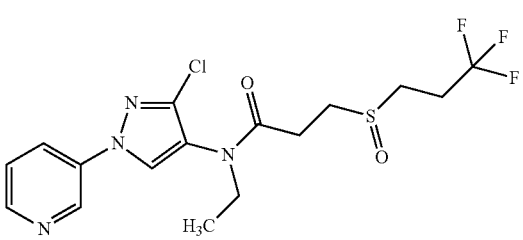 [SMILES: CCN(C(=O)CCS(=O)CCC(F)(F)F)c1cn(-c2cccnc2)nc1Cl]

2. The composition of claim 1, wherein the chloride channel activator compound comprises the avermectins-based compound.

3. The composition of claim 1, wherein the chloride channel activator compound comprises the milbemycins-based compound.

4. The composition of claim 1, wherein the chloride channel activator compound comprises at least one of abamectin, emamectin benzoate, lepimectin, and milbemectin.

5. The composition of claim 1, wherein the chloride channel activator compound comprises emamectin benzoate.

6. The composition of claim 1, further comprising a phytologically-acceptable inert carrier.

7. The composition of claim 1, further comprising an additive selected from a surfactant, a stabilizer, an emetic agent, a disintegrating agent, an antifoaming agent, a wetting agent, a dispersing agent, a binding agent, dye, filler, or combinations thereof.

8. The composition of claim 1, further comprising one or more compounds having acaricidal, algicidal, avicidal, bactericidal, fungicidal, herbicidal, insecticidal, molluscicidal, nematicidal, rodenticidal, virucidal or combinations thereof properties.

9. The composition of claim 1, further comprising one or more compounds that are antifeedants, bird repellents, chemosterilants, herbicide safeners, insect attractants, insect repellents, mammal repellents, mating disrupters, plant activators, plant growth regulators, synergists, or combinations thereof.

10. The composition of claim 1, wherein a weight ratio of the pesticide selected from (I), (II) or any agriculturally acceptable salt thereof to the chloride channel activator compound is no more than about 2048:1.

11. The composition of claim 1, wherein a weight ratio of the pesticide selected from (I), (II) or any agriculturally acceptable salt thereof to the chloride channel activator compound is no more than about 256:1.

12. The composition of claim 1, wherein a weight ratio of the pesticide selected from (I), (II) or any agriculturally acceptable salt thereof to the chloride channel activator compound is no more than about 64:1.

13. The composition of claim 1, wherein a weight ratio of the pesticide selected from (I), (II) or any agriculturally acceptable salt thereof to the chloride channel activator compound is no more than about 32:1.

14. The composition of claim 1, wherein a weight ratio of the pesticide selected from (I), (II) or any agriculturally acceptable salt thereof to the chloride channel activator compound is no more than about 16:1.

15. The composition of claim 1, wherein the weight ratio of the pesticide (I), (II), or any agriculturally acceptable salt thereof and the chloride channel activator compound is X:Y; wherein,
X is the parts by weight of the pesticide (I), (II), or any agriculturally acceptable salt thereof, and the numerical range is $0<X\leq20$;
Y is the parts by weight of the chloride channel activator compound, and the numerical range is $0<Y\leq20$.

16. The composition of claim 15, wherein the ranges of weight ratios of the pesticide (I), (II), or any agriculturally acceptable salt thereof and the chloride channel activator compound are $X_1:Y_1$ to $X_2:Y_2$, wherein one of the following conditions is satisfied:
(a) $X_1>Y_1$ and $X_2<Y_2$; or
(b) $X_1>Y_1$ and $X_2>Y_2$; or
(c) $X_1<Y_1$ and $X_2<Y_2$.

17. A method of controlling pests comprising applying the pesticidal composition of claim 1, near a population of pests, in an amount sufficient to control the pests.

18. The method of claim 17, wherein the chloride channel activator compound comprises the avermectins-based compound.

19. The method of claim 17, wherein the chloride channel activator compound comprises the milbemycins-based compound.

20. The method of claim 17, wherein the chloride channel activator compound comprises at least one of abamectin, emamectin benzoate, lepimectin, and milbemectin.

21. The method of claim 17, wherein the chloride channel activator compound comprises emamectin benzoate.

22. The method of claim 17, wherein the pests comprise sap feeding insects, chewing insects, or both.

23. The method of claim 17, wherein the pests comprise at least one of diamondback moth, *Plutella xylostella*; South American brown stink bug, *Euschistus heros*; and Western plant bug, *Lygus Hesperus*.

24. A method for protecting a plant from infestation and attack by pests, the method comprising contacting the plant with the pesticidal composition of claim 1.

25. The method of claim 24, wherein the chloride channel activator compound comprises the avermectins-based compound.

26. The method of claim 24, wherein the chloride channel activator compound comprises the milbemycins-based compound.

27. The method of claim 24, wherein the chloride channel activator compound comprises at least one of abamectin, emamectin benzoate, lepimectin, and milbemectin.

28. The method of claim 24, wherein the chloride channel activator compound comprises emamectin benzoate.

* * * * *